(12) United States Patent
Kraft

(10) Patent No.: US 6,289,288 B1
(45) Date of Patent: Sep. 11, 2001

(54) METHOD OF DETERMINING MEASURED GAS DATA WITH REMOTE SENSORS

(75) Inventor: Clifford H. Kraft, Naperville, IL (US)

(73) Assignee: Chelsea Group LTD, Itasca, IL (US)

( * ) Notice: Subject to any disclaimer, the term of this patent is extended or adjusted under 35 U.S.C. 154(b) by 0 days.

(21) Appl. No.: 09/259,582

(22) Filed: Mar. 1, 1999

(51) Int. Cl.$^7$ ................................................. G01N 30/88
(52) U.S. Cl. ..................... 702/23; 436/164; 340/632; 250/343; 204/401; 73/23.2
(58) Field of Search ..................... 702/22–24, 27, 702/32, 33, 45, 50, 55, 85, 100, 183, 188, 56; 204/401; 73/24.06, 23.2, 19.01; 205/763; 313/297, 581, 599; 340/632; 324/76.24; 422/83, 90–98; 438/149, 153; 700/266; 250/343; 436/164

(56) References Cited

U.S. PATENT DOCUMENTS

| | | | |
|---|---|---|---|
| 5,464,982 | * 11/1995 | Drucker et al. | 250/343 |
| 5,667,651 | * 9/1997 | Bryan | 204/401 |
| 6,037,592 | * 3/2000 | Sunshine et al. | 250/343 |
| 6,096,560 | * 8/2000 | Scripca et al. | 436/164 |
| 6,169,488 | * 1/2001 | Ketler | 340/632 |
| 6,182,497 | * 2/2001 | Krajci | 73/23.2 |

* cited by examiner

Primary Examiner—Marc S. Hoff
Assistant Examiner—Khoi Duong
(74) Attorney, Agent, or Firm—Clifford Kraft

(57) ABSTRACT

A method of determining remote gas concentration values from remote gas sensors. The method is particularly applicable to heated metal oxide sensors; however, it is not restricted to this type of sensor. A polynomial fit is made of a sensor's gas response curve for each sensor in the system. Usually this is a third order polynomial; however, any other order can be used. The sensors response at zero concentration is a zero or root of the polynomial. This root is factored out of the polynomial reducing it one degree. It is possible to factor out more than one real root if such a root is known further reducing the order of the polynomial. The coefficients of the reduced polynomial are scaled and stored as absolute values in binary words at the remote. At least one additional word is used to store exponents and signs. These words are transmitted to a central location on demand so that the gas response curve can be recreated.

At the central unit, a running or weighted average is used when the reported values are less than the known sensor zero. This average is used to estimate the actual current zero of the sensor. Incoming gas values greater than zero are adjusted for any zero offset determined by the running or weighted average. This compensates for drifting of the actual sensor zero value.

20 Claims, 5 Drawing Sheets

METHOD OF DETERMINING MEASURED GAS DATA WITH REMOTE SENSORS

BACKGROUND

1. Field of the Invention

This invention relates generally to the field of trace gas measurement and more particularly to a method of determination of actual gas values by storing and transmitting polynomials.

2. Description of Related Art

Remote gas sensor units are known in the art and can communicate measured gas concentration values over cables, powerline carrier, or RF systems back to a central location. However, various sensor types including heated metal oxide sensors have a tendency to drift and may require postprocessing to determine accurate gas concentrations. Therefore, if a remote unit simply reports a simple concentration determined by, say sensor resistance, the value reported may not be accurate.

Prior art systems containing remote sensors have typically reported either a derived gas concentration value based an empirical formula relating sensor resistance, or conductance, to concentration, or have just reported a raw resistance or conductance value back to a central location where a formula, or some empirical, method is used to compute gas concentration.

What is badly needed is a method of computing gas concentration values from measured sensor values in the presence of drift and variations caused by ambient temperature or humidity. In addition, the method should make it easy to perform such computations at the central location in systems where there are numerous remotes. The method must account for calibrated sensor and electronic conditions in each remote without putting an overwhelming computation burden on the remote.

SUMMARY OF THE INVENTION

The present invention relates to a method of determining remote gas concentration values from remote gas sensors. The method is particularly applicable to heated metal oxide sensors; however, it is not confined to that type of sensor and can be used with any remote gas sensor.

The method attempts to divide the computational load between the remote unit and a central unit with more computational power. The method can account for sensor drift, variations in remote electronics due to changes in ambient conditions such as temperature and humidity, and can make use of a central unit with tremendously more computational power than that of a remote which may contain only a minimum controller.

The method and apparatus of the present invention can fit local amplifier and electronics responses with polynomials to determine estimated sensor resistance (or some other sensor parameter such as conductance, capacitance, or inductance). The estimated sensor output value can then be transmitted to a central unit for processing where it can be corrected for local temperature and humidity at the remote unit (if the remote unit also transmits such data), and then the received value can be used as part of a statistical process to estimate what the correct current zero point of the sensor should be. A corrected output value can be derived, and used to get actual gas concentration by a system of fitted polynomials for the sensor that were generated during calibration. Since each remote has different calibration polynomials, they can be stored in the remote. The present invention provides a way that each remote can store and transmit the coefficients of its calibration polynomials, when requested, to the central unit. The method provides a way of storing and transmitting polynomial coefficients of any sign or order of magnitude in fixed length words without the normal scaling problems.

DETAILED DESCRIPTION

Figure 1:
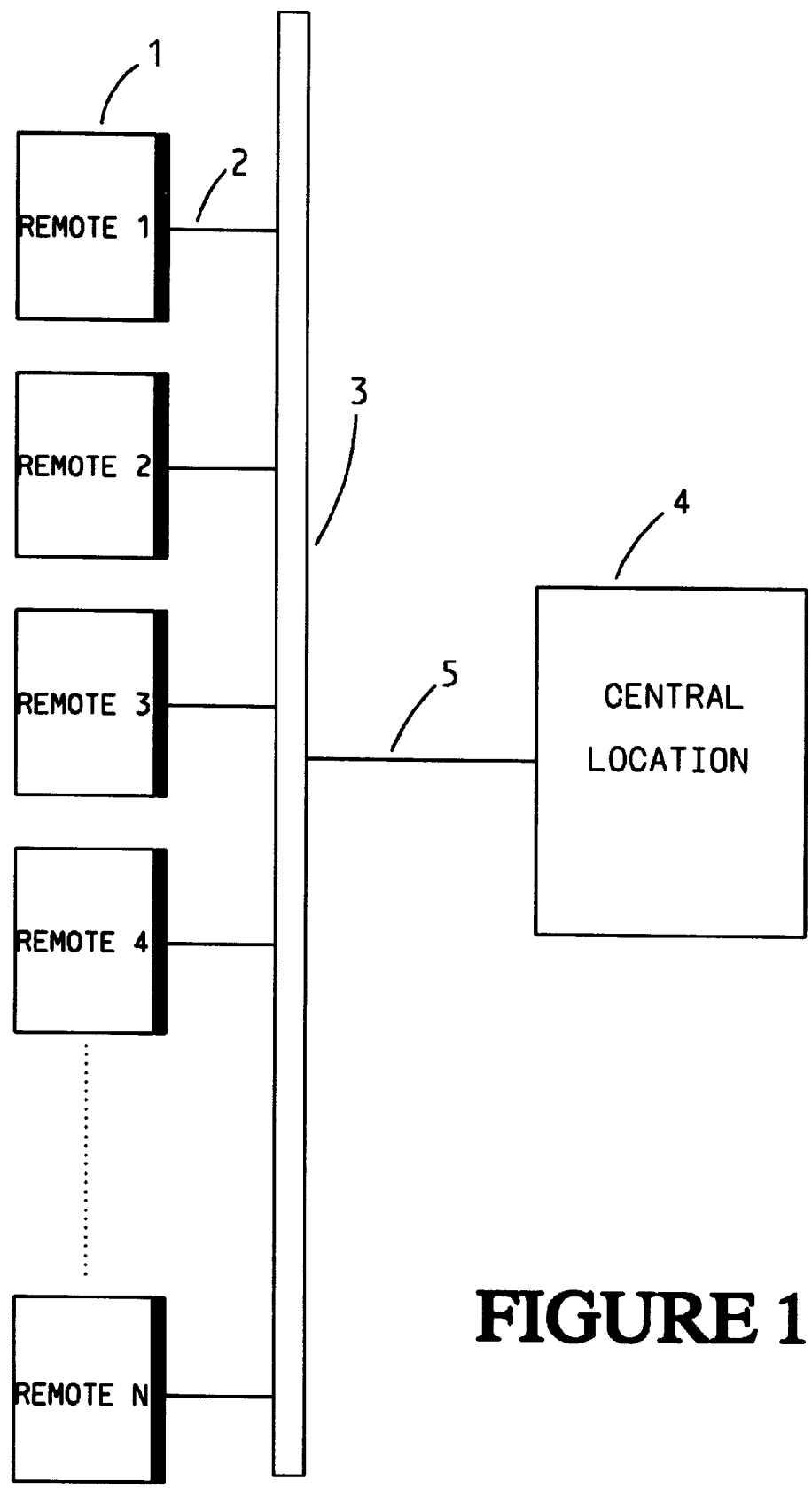
FIG. 1 shows a block diagram of a typical remote gas concentration measuring system.

Turning to FIG. 1, several remote units 1 can be seen. Each remote unit contains at least one target gas sensor. A target gas can be carbon monoxide, carbon dioxide, halogen gases, hydrogen sulphide, methane, ethane, oxygen, hydrogen, nitric and nitrous oxides, hydrogen chloride and any other gas, inorganic or organic, as well as organic vapors. As stated, a target gas within the meaning ascribed here can be any vapor, organic or inorganic, such as the vapor of an organic solvent like trichloroethylene, toluene, benzene, or an inorganic vapor such as hot sulfuric acid. Any gas or vapor falls within the definition of target gas as it applies to the present invention.

The remote unit 1 is connected into a common communications network 3 via a local connection 2, The common communications network 3 is connected to a central location 4 also via a local connection 5. The common communications network can be cable, power line carrier, wireless, optical, optical fiber, or any other communications means. It may lie entirely within a given building or structure, or it may span different, even numerous, buildings, including buildings in different cities. It may also include the common carrier telephone plant, the internet, satellite links, or any other communications means. Within a single building, the preferred method of communications is by powerline carrier. Here signals are transmitted directly over building power wiring. The common communications network also may be a combination of different parts, each comprising any of the different methods communications mentioned.

While the remote unit 1 can contain any type of gas sensor, a typical type of sensor encountered is a hot metal oxide sensor. In this type of sensor, a specially doped piece of metal oxide is heated to around 400 degrees C. At this temperature, its electrical resistance or conductance becomes a function of gas concentration of certain target gases and thus takes on a sensor output value based on concentration. The sensor is targeted to specific gases by choosing its base composition (the type of oxide) and its doping.

Figure 2A:
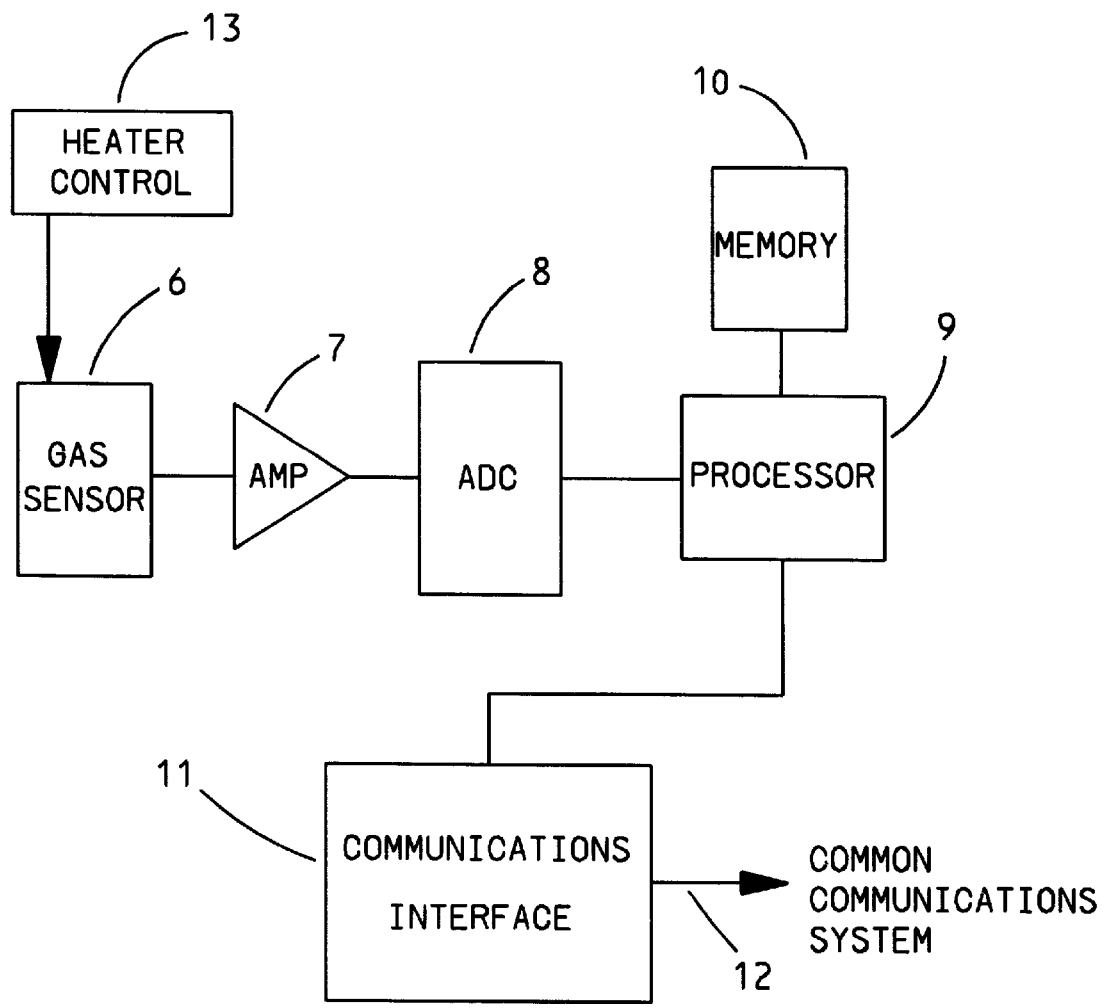
FIG. 2A shows a remote unit with a target gas sensor.

FIG. 2A shows a representative remote gas sensing unit. A gas sensor 6 senses an atmosphere for a target gas. If it is a heated metal oxide sensor, a heater control circuit 13 maintains its temperature. If this is a heated metal oxide sensor, it can be similar to sensors made by Capteur Ltd. or Figaro Corp. The heat control process may or may not involve digital processing. The resistance or conductance of the sensor 6 can be converted to an analog voltage output value by an amplifier/converter circuit 7, such as any standard operational amplifier known in the art (manufactured such as Texas Instruments, Burr Brown), and that voltage can be coupled to an analog to digital (A/D) converter 8 where it is converted to a scaled digital word. Analog to digital convertors can be 12 bits, or any other value above 8 bits such as the Maxim MAX186. This digital word thus becomes a digital version of the output value (which can also be called simply an output value). The digital word can be read by a processor 9, such as the Motorola 68HC05 family or any other processor or microcontrolloer, or other circuit, and transmitted over a common communications system 12 by a communications interface 11. The communications interface can be a powerline carrier transmitter/receiver such as those made by Echelon Corp. The unit can also contain memory 10 in the form of ROM or flash (electrically erasable) memory known in the art, or any other type of memory. Memory of this type is made by National Corp. and many other semi-conductor manufacturers. This memory 10 can contain digital words that represent the coefficients of a calibration polynomial that approximates the gas response curve of the sensor 6.

Figure 2B:
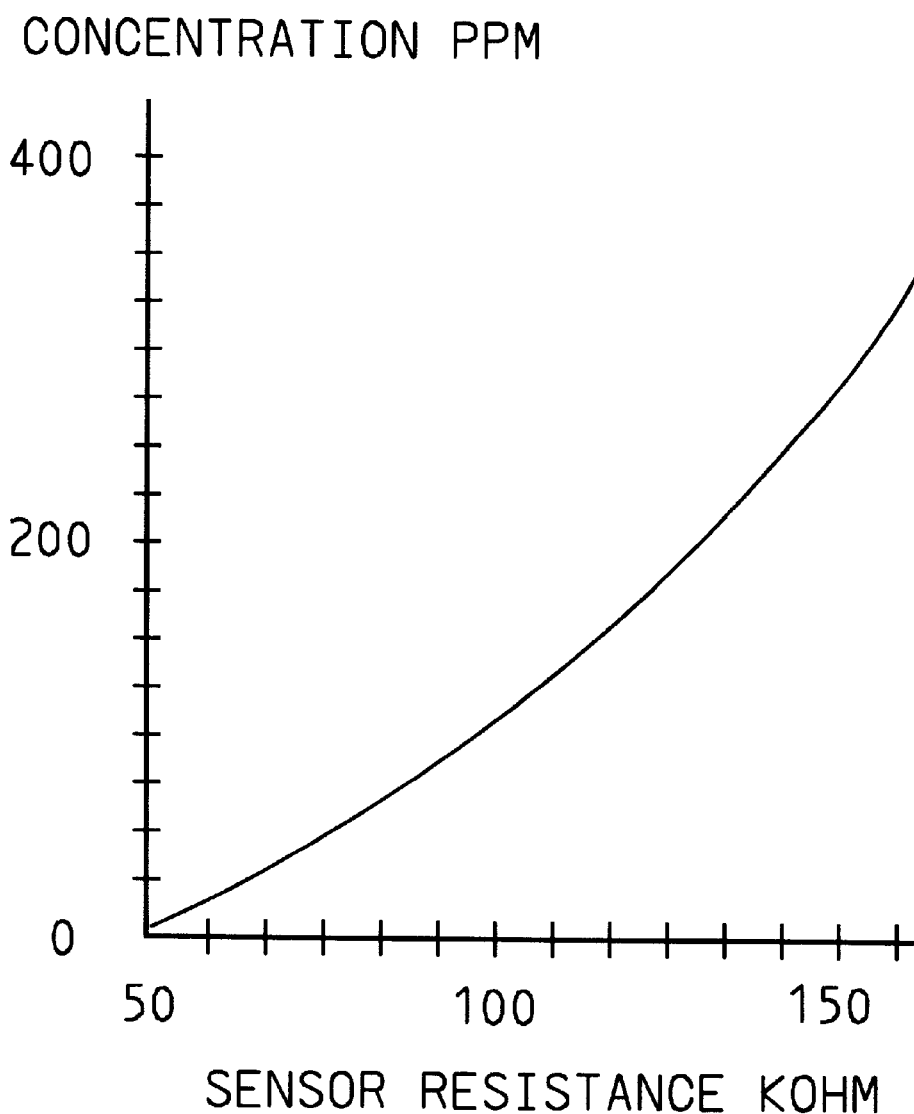
FIG. 2B shows a gas sensor response curve and the polynomial that approximates it.

FIG. 2B shows a graph of a representative metal oxide sensor gas response curve, in this case a carbon monoxide sensor. The horizontal axis represents sensor resistance in k ohms. The vertical axis represents corresponding target gas concentration in parts per million (ppm). FIG. 2B also shows a third order polynomial that approximates this curve. In this polynomial, CO is the gas concentration in ppm, and x is the sensor resistance in k ohms. The coefficients of this polynomial or a similar polynomial representing the conversion from sensor output value to gas concentration can be stored at the remote sensor or sensor location.

A third order polynomial contains four coefficients. To store and transmit such a polynomial conveniently, it is desirable to scale it or code it in a way that any magnitude of coefficient can be handled. It is very desirable to store the coefficients as digital words in a memory such as a ROM or flash ROM previously described. It is possible to use fixed point scaling with such a polynomial; however, this severely limits the magnitude range that can be handled. A much preferable way is to store the polynomial coefficients in a floating point format where digits that represent signs and exponents are stored separately from digits that represent mantissas. It is possible to store signs and exponents in a separate word; however a third order polynomial would then require five digital words to store its four coefficients.

The present invention includes a method that allows a third order polynomial to be stored in a floating point format in four 16 bit words providing one root of the polynomial is known. For example in FIG. 2B, it can be clearly seen that the polynomial crosses 0 ppm concentration around 52 k ohms. If each remote sensor is precalibrated or adjusted so that its zero gas concentration point occurs at the same resistance or conductance (output value) as all the other remote sensors in a system, then that predetermined, or known, zero concentration output value does not need to be stored or transmitted. In the example of FIG. 2B, that known value would be 52 k ohms (or simply 52 with k ohms being understood). Any predetermined value of sensor resistance or conductance can be used as the known zero value provided the sensor can be adjusted to this value for zero ppm gas concentration, and provided that this value lies in a range values where the sensor is sensitive enough to the target gas. It should be noted that the example given is to simply illustrate the functioning of the present invention. The present invention can operate with any value of zero point.

A sensor output value that represents zero gas concentration is a zero of the polynomial that is used to represent the sensor response curve (that means the polynomial's graph passes through zero at that point). It is well known mathematically that if q is a zero of a polynomial P(x), then x−q is a factor. Hence x−q can be factored out of the third order polynomial leaving only a second order polynomial to store, the root being implicitly known at both the remote sensor and at the central location. Thus a floating point version of the (now second order) polynomial can be stored and transmitted in four binary words. While any length words can be used, it has been found that the preferred word length is 16 binary bits.

If a third order polynomial is:

$$P(x)=\alpha x^3+\beta x^2+\gamma x+\delta$$

and Rx is a root, then:

$$P(x)=(x-R_x)(Ax^2+Bx+C)$$

The three values that need to be stored and transmitted are [A, B, C]. Of course, the root Rx must be known. To recover the original third order polynomial coefficients:

$$\alpha=A$$

$$\beta=(B-R_xA)$$

$$\gamma=(C-R_xB)$$

$$\delta=-R_xC$$

If the absolute values of the original coefficients are bounded so that they are never larger in magnitude than the maximum value of an N bit word (such as 16 bits with maximum value of 65,536), the three coefficients of the second order factor can be scaled to be as large as possible (for maximum precision) and still lie between 0 and the maximum (0 and 65,536 for example). The signs of the exponent will always be positive. Hence there is no need to store any exponent sign as is normally done in a floating point representation. With gas sensor coefficients encountered in the field, the exponent will always lie between 0 and 16, so 4 binary bits will suffice to store each exponent. The reduced second order factor has three coefficients, and will thus need 12 bits to store exponents. This leaves 4 bits remaining in a 16 bit word to store the three signs of the coefficients. Since only 3 bits are needed, there is an extra bit that may be used for signalling or other purpose, or simply ignored.

At a central location, the three coefficients can be descaled and re-signed, and then expanded back into the original set of four coefficients of the actual third order polynomial by use of the known root. This can occur whenever an output value is received and needed to be converted into a gas concentration, or alternatively, the original polynomial can be reconstructed one time at the central location and stored as a set of four floating point coefficients.

The preferred method is to calibrate a given sensor by recording its output value for various gas concentration values. The resulting sensor curve is then fitted by a third order, or other order (including first order for some sensors), polynomial using standard regression techniques. The curve is adjusted or offset if necessary to place its zero concentration value on some predetermined polynomial root. The third order polynomial can then be factored, and the resulting second order coefficients scaled and stored along with a sign and exponent word at the remote sensor location. In the preferred method, four 16 bit binary words could be used for this purpose. However, the use of 16 bits is not essential for the present invention; any length binary word would be within the scope of the invention. Also, any higher order polynomials can be used to represent sensor response curves. They can be reduced in order by factoring out known roots.

Figure 3:
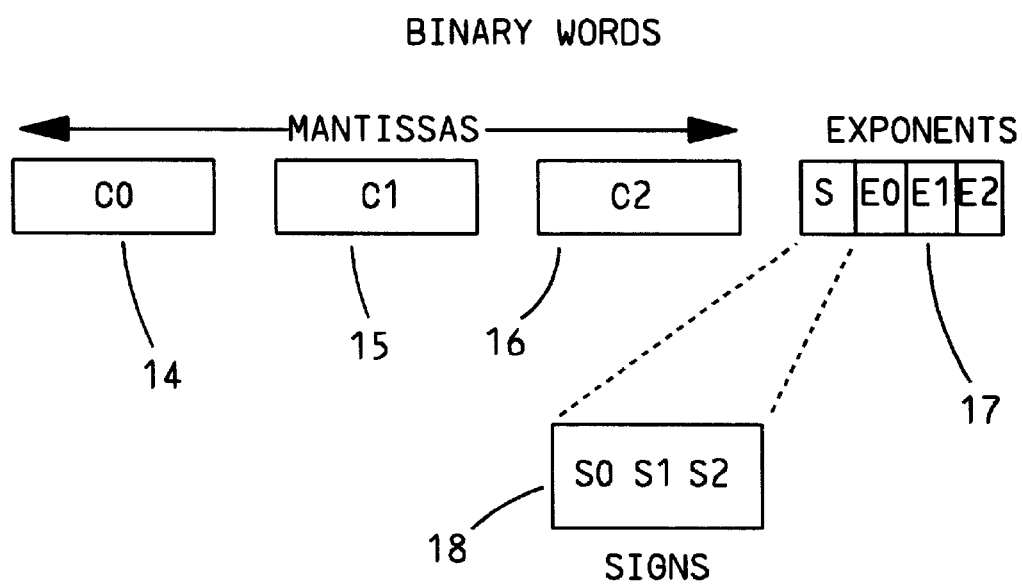
FIG. 3 shows a method for storing compressed polynomials.

FIG. 3 shows a possible way of storing polynomials that have been compressed from third order polynomials to second order polynomials as previously described. Mantissas of the coeffi-cients C0, C1, and C2 are stored in binary words 14, 15, 16. A fourth binary word 17 is used to store the positive exponents E0, E1, and E2 as well as the signs of C0, C1, and C2. The particular sub-word or byte that contains these signs is expanded in FIG. 3 18 so that the signs S0, S1, and S2 can be seen. The preferred method is to use 16 bit words with the signs contained in one 4 bit byte 18. In this case, one bit of that byte 18 is not used, or can be used for another purpose. Embodiments of the present invention using polynomials of order different from three would use a similar procedure.

Each remote sensor in a system can undergo a similar calibration procedure, and a unique polynomial can be stored in each remote sensor according to the method described above. As each sensor comes online and into communications with the central location, it can transmit the four (or more) words representing its stored polynomial. Usually it is only necessary to transmit this polynomial once when the remote unit comes online; however, systems which transmit the polynomial more than once are within the scope of the present invention.

As one or more central locations receive the polynomials, they can be converted back to the original higher order polynomials through the use of the known root, or roots, that is(are) common to all the remote units as described above. Then, in operation, as sensor output values are received from each sensor, they can be converted into gas concentration values using the polynomial corresponding to the particular remote sensor where the output value came from. Systems using dynamic calibration techniques could recompute new polynomials and transmit them the other direction for storing at the remote units. Systems using static calibration would only update remote polynomials when a new calibration occurs.

At a central location, it is possible to take precautions against possible drift of the sensor zero point. If a sensor drifts to a value that would be considered below zero gas concentration, reports of this value can be used to form a running average or a weighted average so that an estimate or prediction can be made of the sensor's behavior. In particular, it is possible with a running or weighted average to compute a single number value that accurately represents the sensor's current estimated zero value, provided that readings are actually being taken in zero gas conditions. The present invention augments this running or weighted average as long as readings are being reported that are below the known zero point (the zero of the above discussed polynomial).

When any sensor output value comes in that is above the known zero point, the averaging process is stopped and held, and the reading is adjusted, or offset by the estimated zero point (the result of the running average or a prediction of a weighted chain of previous values that were below the known zero). An estimated correction is formed by subtracting the estimated zero point from the known zero point (zero of the polynomial). A corrected output value is then formed by adding the estimated correction to the incoming output value (adjusted by the sensor's behavior during the last time period when it was reading at or below the known zero value). This corrected output value can be then used as an independent variable in the sensor polynomial to compute a final estimate of gas concentration.

In the present invention, as long as the currently reported sensor output value remains above the known zero value, gas concentrations are reported based on the corrected output value generated from the previous running or weighted average result. When the incoming sensor output values again drop to, or below, the known zero, the process of statistically estimating the current zero value is re-started (and zero concentration is reported). The running or weighted average process then again continues until the incoming sensor output value increases above the known zero point again (if it ever does). This process yields a more accurate gas concentration estimate when the sensor has drifted below the point it was adjusted to during calibration If the sensor drifts the opposite way (upward), this method cannot improve accuracy (indeed it should be stopped) since there is no way to distinguish between an upward drift of the zero point and an actual increase in gas concentration (without using some sort of dynamic or static re-calibration).

Figure 4:
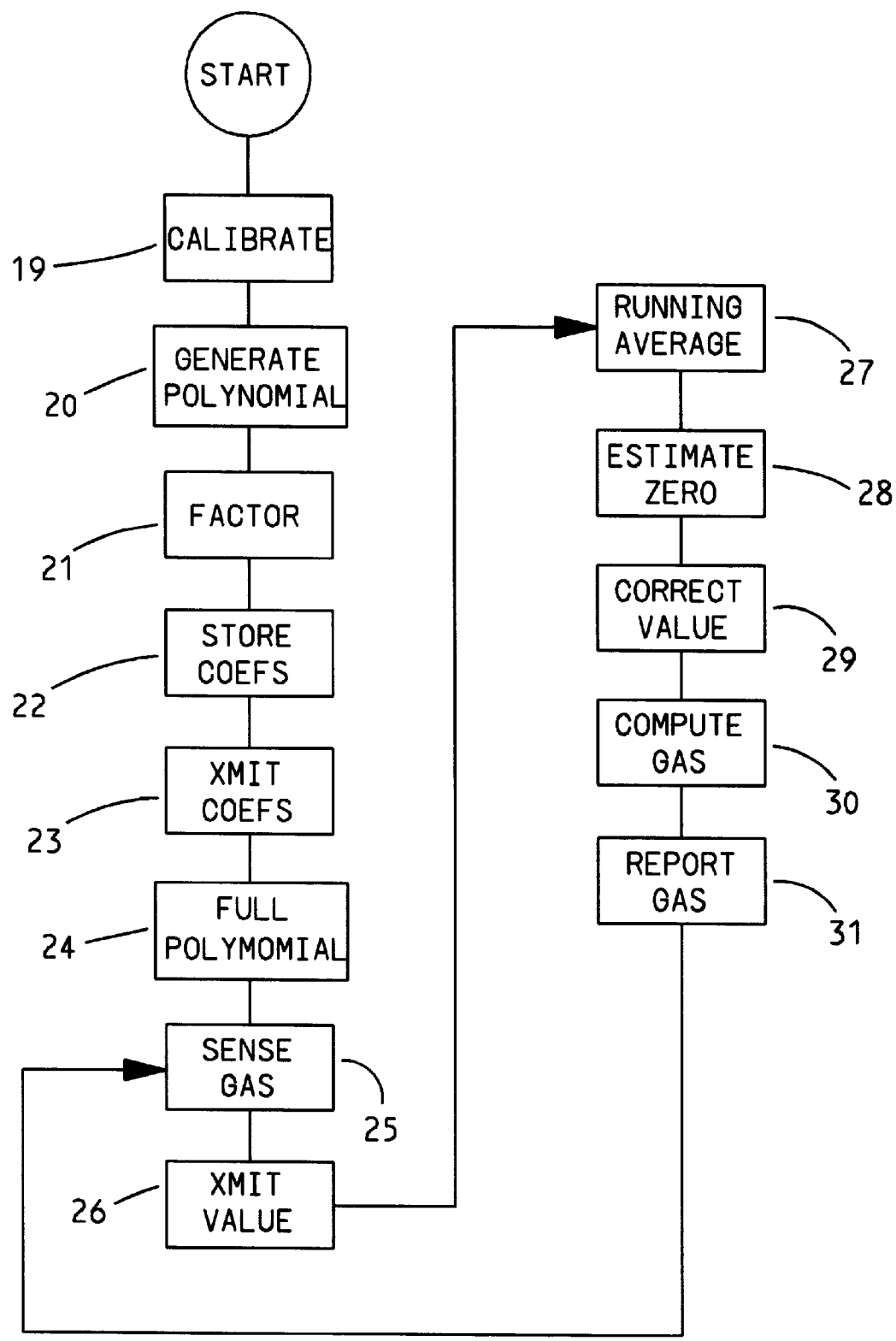
FIG. 4 shows a flowchart of a method of computing actual gas concentrations from sensor output values and polynomials.

FIG. 4 shows a flowchart of a method of the present invention. A given gas sensor is first calibrated 19 and a polynomial representing that calibration is generated 20. The polynomial is factored 21 to reduce its order as previously described. The coefficients of the reduced polynomial are stored 22 as well as the exponents and signs. On demand from the central location, these coefficients, exponents, and signs are transmitted 23 via powerline, cable, RF, light, fiber optic, or any other method of communication or transmission. At a central location, the full polynomial is reconstructed 24 from the transmitted coefficients of the reduced polynomial and the known root or zero value.

In operation, the sensor continually senses the atmosphere surrounding it for the target gas 25. When demanded, it transmits an output value 26 of resistance, conductance or other quantity to the central location. If this output value is below the known zero value or root, an optional running or weighted optional running or weighted average 27 or chained estimate can be made of the actual zero value of the sensor. A chained estimate is simply the weighted average over a finite sequence of previously stored output values which can optionally be used either as an estimator or a predictor. The sequence can optionally be weighted to give more importance to recent values then to older values. This running average or estimate is used to estimate the actual current sensor zero value 28. With this estimate, the current output value can be corrected for downward sensor drift 29 (at or below zero). This corrected value is then used with the polynomial to compute the gas concentration 30 which is reported or stored 31. The process can then repeat with gas sensing 25 and reporting of the next output value 26. An example of this process is:

$$Q = \sum_{i=1}^{N} w_n k_n$$

where wn is a weight proportional to sample age and kn is a sample

It should be noted that an alternate embodiment of the present invention omits the steps of computing an average 27, estimating a zero value 28 and correcting the current output value 29. In this embodiment, no compensation is made for sensor drift.

Other embodiments of the invention could compensate for positive (upward) sensor drift as well as negative (downward) drift. In these embodiments, a method of dynamic re-calibration could be used where the sensor is exposed to a controlled atmosphere in the field from time to time and its actual zero point in this known zero gas concentration is adjusted to match the desired known zero point.

While the preferred embodiments of the present invention have been shown and described, it is to be understood that various modifications and changes could be made thereto without departing from the scope of the appended claims.

I claim:

1. A method of computing actual gas concentration in a system with remote gas sensors comprising the steps of:

storing precomputed coefficients of a gas calibration polynomial at a remote gas sensor;

transmitting said coefficients to a central location;

sensing a target gas with said remote gas sensor to produce an output value;

transmitting said output value to said central location;

adding a predetermined value to said output value to form a modified output value;

solving a polynomial equation from said coefficients and said modified output value to determine a gas concentration value.

2. The method of claim 1 further comprising the steps of:

comparing said output value against a threshold;

forming an estimated zero point from said output value and previously reported output values when said output value is less than said threshold;

subtracting said estimated zero point from a known zero point to produce an estimated correction;

using said estimated correction as said predetermined value for adding to said output value to form said modified output value.

3. The method of claim 1 wherein said gas calibration polynomial is a third order polynomial.

4. The method of claim 1 wherein said remote unit transmits said polynomial coefficients and said output value over a powerline carrier system.

5. The method of claim 1 wherein said coefficients of said gas calibration polynomial are compressed by factoring out at least one known root and keeping coefficients of a resulting lower order polynomial.

6. The method of claim 5 wherein the coefficients of said lower order polynomial are each scaled and contained in a set of binary words with scale factors and signs of said coefficients being contained in at least one additional binary word.

7. The method of claim 6 wherein said binary words contain 16 bits.

8. The method of claim 6 wherein said binary words and said additional binary word are transmitted from said remote gas sensor to said central location.

9. The method of claim 8 wherein said binary words are transmitted by a powerline carrier system.

10. A method of computing actual gas concentration in a system with remote gas sensors comprising the steps of:

storing precomputed coefficients of a gas calibration polynomial at a remote gas sensor;

transmitting said coefficients to a central location;

sensing a target gas with said remote gas sensor to produce an output value;

transmitting said output value to said central location;

comparing said output value against a threshold;

forming an average from said output value and previously reported output values when said output value is less than said threshold;

using said average to compute an estimated zero point;

subtracting said estimated zero point from a known zero point to form an estimated correction;

adding said estimated correction to said output value to form a modified output value;

solving a polynomial equation from said coefficients and said modified output value to determine a gas concentration value.

11. The method of claim 10 wherein said remote unit transmits said polynomial coefficients and said output value over a powerline carrier system.

12. The method of claim 10 wherein the coefficients of said polynomial are each scaled and contained in a set of binary words with scale factors and signs of said coefficients being contained in an additional binary word.

13. The method of claim 12 wherein said binary words contain 16 bits.

14. The method of claim 12 wherein said binary words and said additional binary word are transmitted from said remote gas sensor to said central location.

15. The method of claim 14 wherein said binary words are transmitted by a powerline carrier system.

16. An apparatus for computing actual gas concentration of a target gas in a system with remote gas sensors comprising:

at least one gas sensor at a remote location with an output value that changes according to gas concentration;

a polynomial stored at said remote location representing a gas response of said remote gas sensor;

a means for transmitting said polynomial to a central location;

a means at said remote location for measuring said gas sensor output value;

a means for transmitting said gas sensor output value to said central location;

a means at said central location for evaluating said polynomial using said gas sensor output value to determine gas concentration.

17. The apparatus of claim 16 wherein the means for transmitting said polynomial and said output value is a powerline carrier system.

18. The apparatus of claim 16 wherein said polynomial is third order.

19. The apparatus of claim 18 wherein said polynomial is stored as a set of binary words.

20. The apparatus of claim 19 wherein said set of binary words contains four members.

* * * * *